(12) United States Patent
Adkins (10) Patent No.: US 7,685,864 B1
(45) Date of Patent: Mar. 30, 2010

(54) MODULAR MANIFOLD FOR INTEGRATED FLUIDICS AND ELECTRONICS

(75) Inventor: Douglas Ray Adkins, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 412 days.

(21) Appl. No.: 11/699,847

(22) Filed: Jan. 30, 2007

Related U.S. Application Data (60) Provisional application No. 60/763,759, filed on Jan. 31, 2006.

(51) Int. Cl.
G01N 30/02 (2006.01)
(52) U.S. Cl. ...................................... 73/23.4
(58) Field of Classification Search .................. 73/23.4
See application file for complete search history.

(56) References Cited

U.S. PATENT DOCUMENTS

| | | | |
|---|---|---|---|
| 5,412,994 A * | 5/1995 | Cook et al. | .................... 73/756 |
| 6,171,378 B1 | 1/2001 | Manginell et al. | |
| 6,379,929 B1 * | 4/2002 | Burns et al. | ................ 435/91.2 |
| 6,772,513 B1 | 8/2004 | Frye-Mason et al. | |
| 6,930,051 B1 | 8/2005 | Manginell et al. | |
| 7,003,405 B1 * | 2/2006 | Ho | ................................ 702/32 |
| 7,098,449 B1 * | 8/2006 | Miller et al. | ................. 250/287 |
| 7,118,712 B1 * | 10/2006 | Manginell et al. | ........... 422/101 |
| 7,168,298 B1 * | 1/2007 | Manginell et al. | .......... 73/54.25 |
| 7,229,593 B1 * | 6/2007 | Ho | ................................ 422/83 |
| 2006/0078475 A1 * | 4/2006 | Tai et al. | ..................... 422/102 |
| 2007/0134667 A1 * | 6/2007 | Ashley et al. | ................... 435/6 |

OTHER PUBLICATIONS

Manginell, Ronald P., et al., *Technical Proceedings of the 1999 International Conference on Modeling and Simulation of Microsystems*; Chpt. 18, MSM 99 (Apr. 19, 1999), pp. 663-666.
Manginell, R. P., "Recent Advancements in the Gas-Phase MicroChemLab", *Proc. of SPIE 5591*, 44, 2004.

* cited by examiner

*Primary Examiner*—Hezron Williams
*Assistant Examiner*—Rodney T Frank
(74) *Attorney, Agent, or Firm*—Kevin W. Bieg; Peacock.Myers, P.C (57) ABSTRACT

An airtight preconcentrator housing and/or a sensor housing for chemical testing, the housing(s) comprising internal dimensions such that a pre-manufactured preconcentrator and/or sensor can be disposed therein. The housings can also comprise electrical contacts disposed therein which align with and thus provide electrical connection to the preconcentrator and/or sensor. The preconcentrator and/or sensor can be easily and quickly replaced.

20 Claims, 7 Drawing Sheets

MODULAR MANIFOLD FOR INTEGRATED FLUIDICS AND ELECTRONICS

CROSS-REFERENCE TO RELATED APPLICATIONS

This application claims priority to and the benefit of the filing of U.S. Provisional Ser. No. 60/763,759 entitled: Modular Manifold for Integrated Fluidics & Electronics, filed on Jan. 31, 2006 and the specification thereof is incorporated herein by reference.

STATEMENT REGARDING FEDERALLY SPONSORED RESEARCH OR DEVELOPMENT

The Government has rights to this invention pursuant to Contract No. DE-AC04-94AL85000 awarded by the U.S. Department of Energy.

BACKGROUND OF THE INVENTION

The present invention relates to a modular micro-chem lab. More specifically, the present invention relates to a hand-held micro-them lab which is preferably pre-fabricated onto a circuit board and which permits preconcentrators and/or sensors to be quickly and easily interchanged.

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Hand-held chemical testing devices employing preconcentrators have been known for sometime. In such devices, a gas or liquid is typically first passed over or through a preconcentrator, which typically comprises a heatable material that is selected based on that material's ability to sorb the chemical to be tested. Accordingly, the selectively sorbent material of the preconcentrator acquires an excess of the chemical to be tested. Upon rapid heating of the preconcentrator, the sorbed chemical is rapidly liberated. Because the preconcentrator is in fluid contact with the sensor, the rapid liberation of the chemical to be tested is seen as a chemical spike on the sensor. The magnitude of the spike is thus directly proportional to the quantity of gas emitted by the preconcentrator.

U.S. Pat. No. 6,772,513 to Frye-Mason et al. describes a chemical microanalytical system which has a preconcentrator and a chemical detector. U.S. Pat. No. 6,171,378 to Manginell et al. also describes a chemical preconcentrator for a hand-held chemical testing device. These and other known chemical sampling and testing devices, however, do not permit a user to rapidly replace the preconcentrator and/or sensor within a sealed environment. The preconcentrator of Frye-Mason et al. for example, provides a single preconcentrator die, which contains not only the selectively sorptive material and the heating element, but also a seal ring. Accordingly each preconcentrator die is further required to also contain a seal ring which must be manufactured and maintained after each use such that the seal ring is kept to exacting tolerances in order to prevent any leakages. Frye-Mason et al. further require that the preconcentrator die be electrically and fluidically glued to the microfluidic substrate by the use of epoxies and/or solders (col. 4, lines 42-60), thus making rapid replacement of such dies impossible.

Because the aforementioned patents, and other known chemical testing devices do not permit the rapid replacement of the preconcentrator and/or sensor within a sealed environment, these and other known devices further require significant down-time when changing the sensor and preconcentrator so that a different chemical can be detected and measured. Still further, because these and other known devices are not designed to be rapidly re-tooled to detect different chemicals, the known testing devices also require a significant amount of re-wiring when changing from one sensor to the next. There is thus a need for a method and apparatus which permits a user to rapidly and effectively replace the preconcentrator and the sensor within a sealed environment and which further requires little or no re-wiring, soldering, or gluing when changing from one sensor and preconcentrator to the next.

BRIEF SUMMARY OF THE INVENTION

An embodiment of the present invention relates to a sensing unit having a sensor which includes one or more electrical pads, and a sensor housing which includes internal dimensions connected to one or more ports, one or more sealing mechanisms, and one or more electrical contacts. The internal dimensions are preferably sufficient to permit the sensor to be disposed therein. The sensing unit can also include a preconcentrator housing and the preconcentrator housing can have internal dimensions, which preferably form a recessed area, connected to one or more ports, and one or more electrical contacts. The internal dimensions are preferably sufficient to permit a preconcentrator to be disposed therein. The internal dimensions of the preconcentrator housing are preferably sealable from an outside environment, except for one or more ports. The internal dimensions of the sensor housing are also preferably sealable from an outside environment, except for one or more ports.

In one embodiment, at least one of the electrical pads of the sensor is preferably configured in a pre-determined manner to substantially align with at least one of the electrical contacts when the sensor is disposed within the internal dimensions, which preferably form a recessed area, of the sensor housing. In one embodiment, a preconcentrator is disposable within said internal dimensions of the preconcentrator housing. The preconcentrator can have one or more electrical pads configured such that they substantially align with one or more electrical contacts within the internal dimensions of the preconcentrator housing.

In one embodiment, the preconcentrator housing is fluidly connected to the sensor housing. The sensing unit can also include a gas chromatograph unit. The sensing unit preferably operates with only a pressure fit between the electrical pads of the sensor and the contacts of the sensor housing, and without the need for the pads of the sensor to be soldered onto the contacts of the sensor housing and without the need for an adhesive or sealant between a surface of the sensor and a surface of the sensor housing.

In one embodiment, the preconcentrator operates with only a pressure fit between the electrical pads of the preconcentrator and the contacts of the preconcentrator housing, and without the need for pads of the preconcentrator to be soldered onto the contacts of the preconcentrator housing and further without the need for an adhesive between a surface of the preconcentrator and a surface of the housing.

The sensor and/or preconcentrator can preferably be replaced by an individual in about a minute or less. In a preferred embodiment, the sensor comprises a standing acoustic wave sensor. The electrical contacts comprised within the sensor housing and/or the preconcentrator housing can comprise resilient electrical contacts.

An embodiment of the present invention also relates to a method for replacing a preconcentrator including at least partially disassembling a preconcentrator housing, removing an existing preconcentrator, installing a new preconcentrator, and reassembling the preconcentrator housing. In one embodiment, the method for replacing a preconcentrator preferably does not include applying a solder or an adhesive.

Disassembling a preconcentrator housing can include removing a top portion of the preconcentrator housing. Installing a new preconcentrator can include aligning electrical pads of the preconcentrator with resilient electrical contacts of the preconcentrator housing. In one embodiment of the method, reassembling the preconcentrator housing preferably encloses the preconcentrator within an airtight chamber fluidly connected to one or more ports.

An embodiment of the present invention also relates to a method for replacing a chemical sensor including at least partially disassembling a sensor housing, removing an existing sensor, installing a new sensor, and reassembling the sensor housing. In one embodiment, the method of replacing a chemical sensor preferably does not include applying a solder or an adhesive.

In one embodiment, disassembling the sensor housing can include removing a top portion of the sensor housing and installing a new sensor can include aligning electrical pads of the sensor with resilient electrical contacts of the sensor housing. Reassembling the sensor housing preferably encloses the sensor within an airtight chamber which is fluidly connected to one or more ports.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by way of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is directed to a chemical sensing apparatus which preferably comprise air-tight housings that can be quickly and easily opened and wherein a pre-manufactured preconcentrator and/or a pre-manufactured sensor can quickly and securely be disposed. The air-tight housings also preferably comprise electrical contacts disposed therein which align with and provide electrical connection to the preconcentrator and/or sensor.

The term "absorb" as used throughout the specification and claims is used for the sake of simplicity and is intended to include any and all manners, methods, and/or combinations thereof wherein a sorbent can attach to a sorptive.

Figure 1:
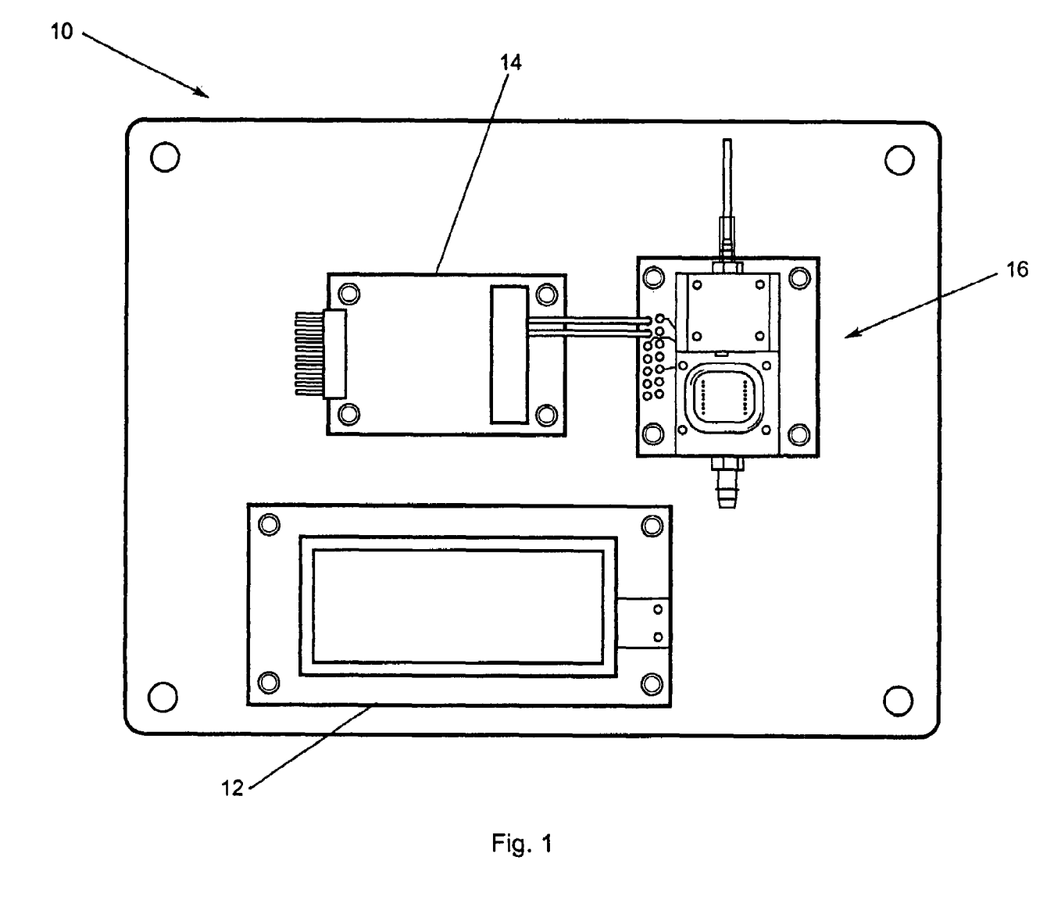
FIG. 1 is a top-view drawing illustrating an embodiment of the chemical test unit of the present invention.

As illustrated in FIG. 1, an embodiment of the present invention relates to chemical test unit 10 which preferably comprises one or more input/output devices 12, a processing unit 14, and sensing assembly 16.

Figure 2:
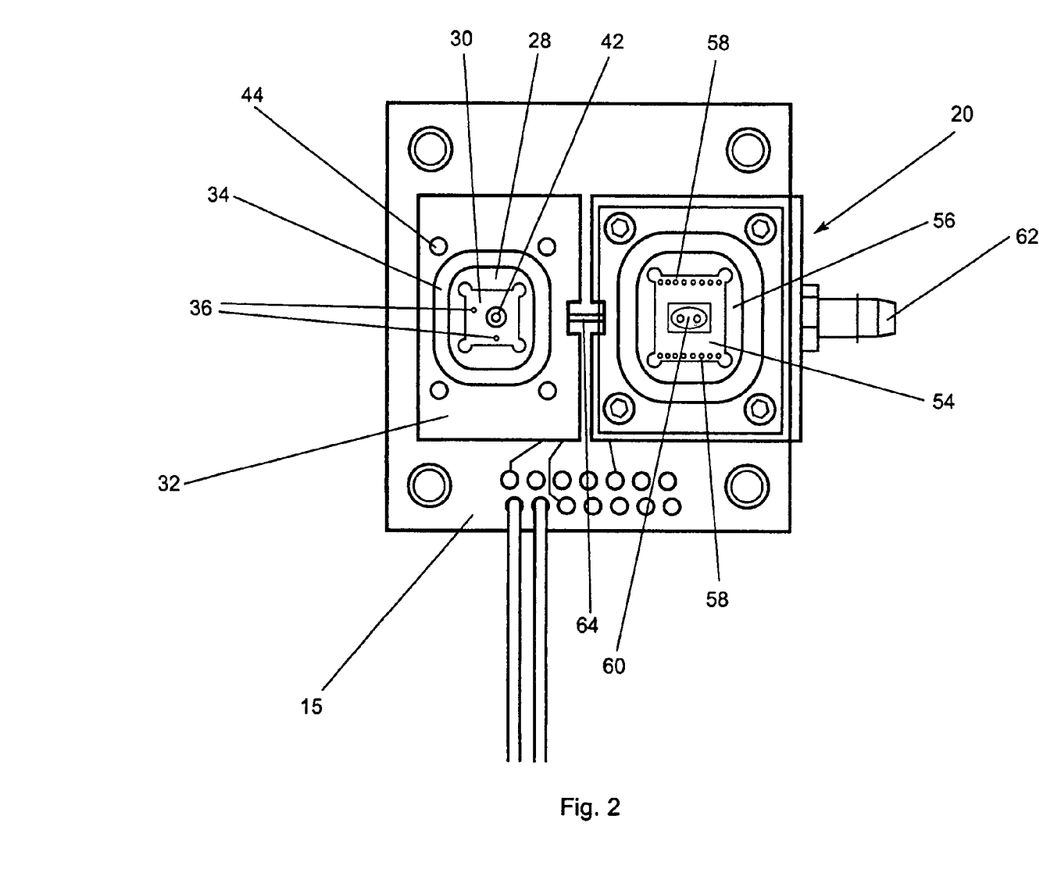
FIG. 2 is a top-view drawing illustrating an embodiment of the sensing assembly of the present invention comprising a preconcentrator housing, a sensor housing, and an accompanying circuit board.
Figure 3:
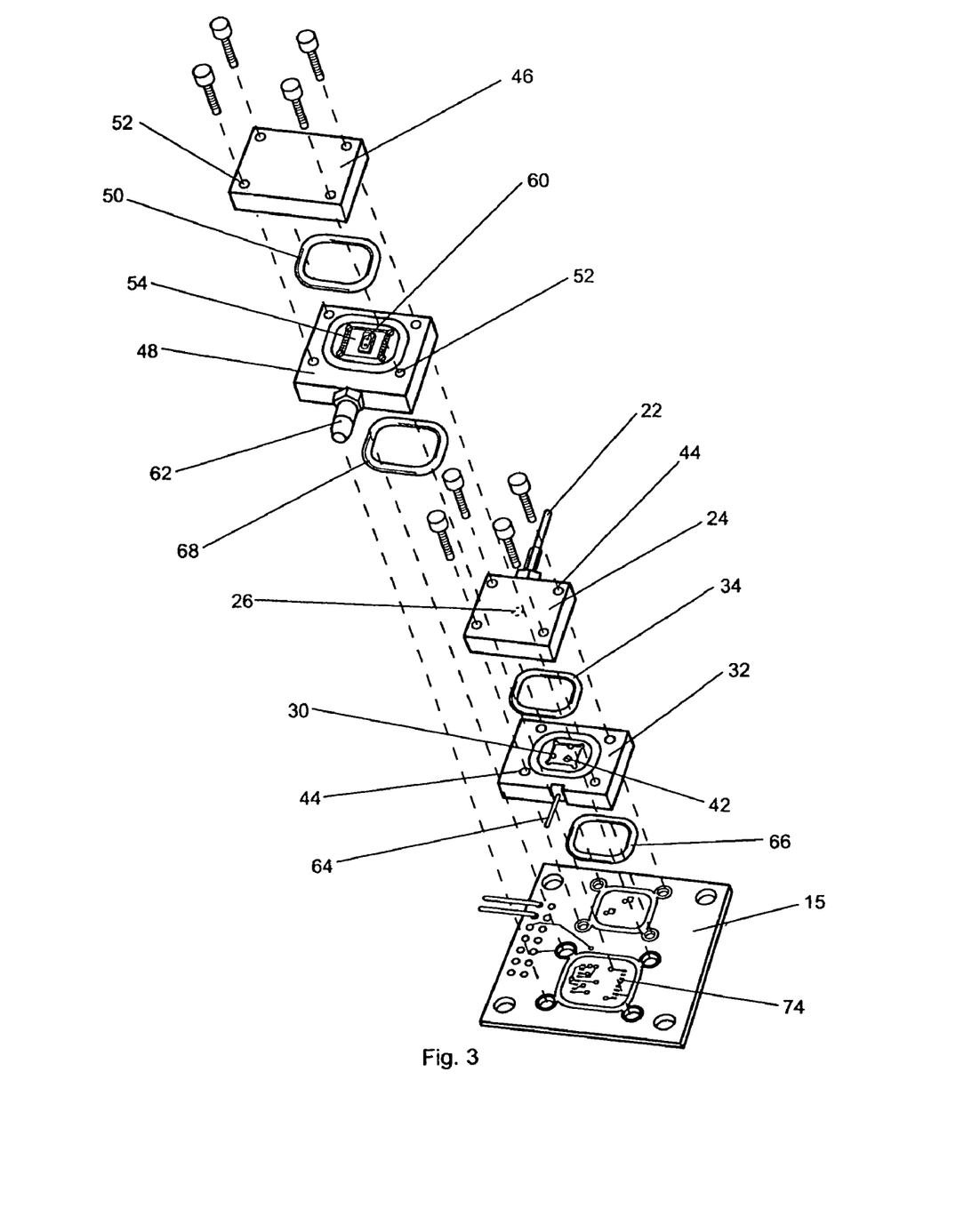
FIG. 3 is an exploded-view drawing illustrating an embodiment of the sensing assembly of the present invention comprising a preconcentrator housing, a sensor housing, and an accompanying circuit board.
Figure 4:
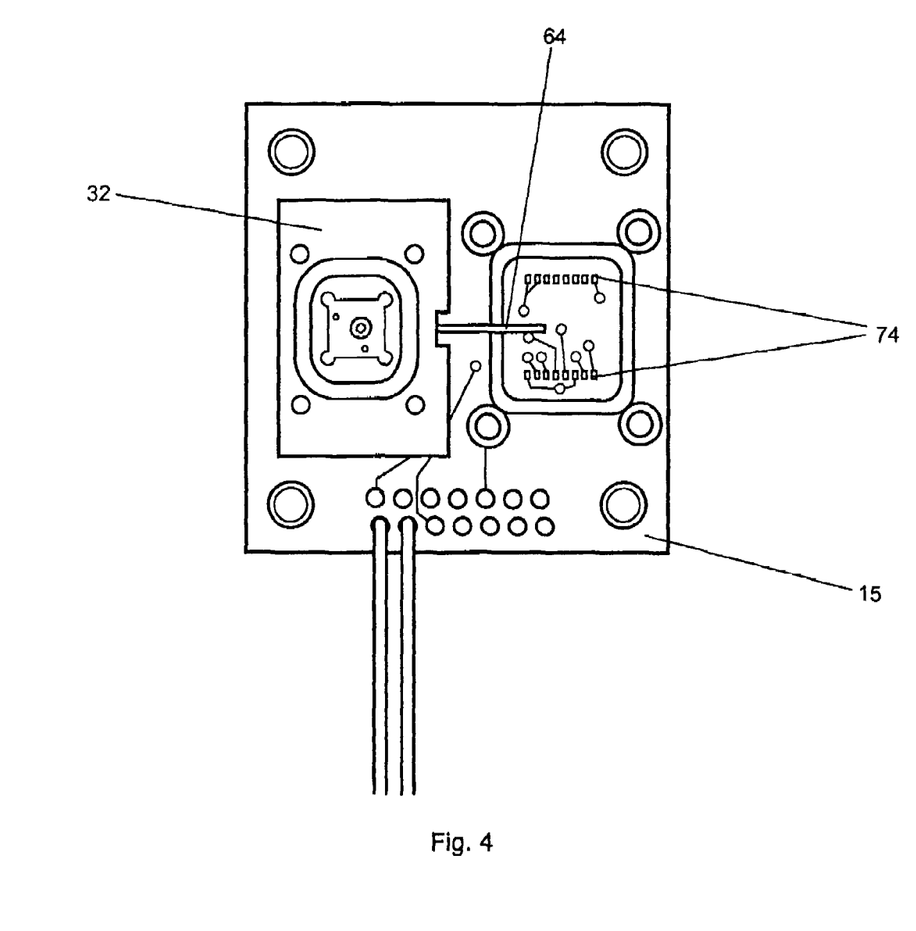
FIG. 4 is a top-view drawing illustrating an embodiment of the sensing assembly of the present invention with the upper half of the preconcentrator removed and with the sensor housing removed to show circuit board contacts.

Sensing assembly 16, illustrated in FIG. 2, preferably includes preconcentrator housing 18, sensor housing 20, and circuit board 15. An exploded-view drawing of sensing assembly 16 is illustrated in FIG. 3. Referring to FIG. 3 specifically, and FIGS. 1-2 and 4-6 generally, preconcentrator housing 18 preferably includes gas/liquid inlet 22 which is preferably connected to, incorporated into, or otherwise formed from upper preconcentrator housing half 24. Internal porting 26 preferably leads from inlet 22 to airtight chamber 28. Airtight chamber 28, preferably includes preconcentrator-holding recess 30 disposed in lower preconcentrator housing half 32. Upon studying this application, those skilled in the art will readily recognize that this recess can be provided within the upper preconcentrator housing half 24 while still providing desirable results. Although airtight chamber 28 is preferably created by providing gasket 34, any manner of creating an airtight chamber known to those skilled in the art can be used and will provide desirable results.

Recess 30 preferably comprises one or more electrical contacts 36. Electrical contacts 36 preferably provide electrical conductivity from electrical pads 38 of preconcentrator 40 to circuit board 15. Internal port 42 is preferably disposed within recess 30 and provides fluid communication between preconcentrator recess 30 and sensor housing 20.

Gasket 34 preferably fits partially within a retaining groove disposed in either upper preconcentrator housing half 24, or lower preconcentrator half 32 and is preferably sandwiched between halves 24 and 32 via one or more fasteners. In a preferred embodiment, one or more fastener holes 44 are optionally provided at least partially through preconcentrator housing 18 such that upper half 24 and lower half 32 can be easily, quickly, and securely connected to one another.

In a most preferred embodiment, preconcentrator 40 is pre-manufactured to a size which fits securely within preconcentrator recess 30. Preconcentrator 40 also preferably has one or more electrical pads 38 which are arranged in a predetermined fashion and are configured to align and make electrical contact with one or more electrical contacts 36. Because preconcentrator recesses 30 of the present invention and preconcentrator 40 are preferably manufactured to a predetermined size and configuration, a user can easily and quickly replace or otherwise swap out a preconcentrator and cause electrical contact to be provided to the newly-installed preconcentrator by simply removing upper half 24, dropping in a new preconcentrator 40, and replacing upper half 24. Because preconcentrator housing 18 is preferably provided within airtight chamber 28, preconcentrators used in the present invention do not each require their own sealing mechanism to be integrally incorporated. Electrical contacts 36 are most preferably spring-loaded or otherwise resilient and are most preferably pin-type electrical contacts, so that consistent electrical contact can be made between them and preconcentrator contact pads 38 while preconcentrator 40 is enclosed within recess 30. Because contacts 36 are preferably spring-loaded or otherwise resilient and can thus obtain sufficient electrical connection simply upon contact with preconcentrator pads 38, no soldering, heating, or other form of connection between contacts 36 and pads 38 is required, thus further facilitating the rapidity and ease with which a preconcentrator may be replaced.

As with preconcentrator housing 18, sensor housing 20 also preferably comprises upper half 46 and lower half 48. Gasket 50 is preferably partially disposed within a retaining groove disposed in either upper sensor housing half 46, or lower sensor housing half 48 and is preferably sandwiched between upper and lower halves 46 and 48 via one or more fasteners. In a preferred embodiment, one or more fastener holes 52 are preferably provided at least partially through sensor housing 20 such that upper sensor housing half 46 and lower sensor housing half 48 can be easily, quickly, and securely connected to one another. Sensor recess 54 is preferably provided within airtight chamber 56 which is most preferably created by gasket 50. However, any other manner known to those skilled in the art for providing an airtight chamber can be provided and can provide desirable results. One or more electrical contacts 58 are also preferably provided within sensor recess 54. Contacts 58 are most preferably spring-loaded or otherwise resilient contacts, and are most preferably pin-type contacts. Internal porting 60 preferably provides fluid connection between internal porting 60 and outlet 62.

In one embodiment, preconcentrator housing 18 and sensor housing 20 are formed at least partially from a common substrate. For example lower halves 32 and 48 can be formed form a single continuous piece of material. In another embodiment, however, preconcentrator housing 18 and sensor housing 20 are separate units. In that embodiment, one or more gas/liquid transporting connectors 64 are preferably disposed preconcentrator housing 18 and sensor housing 20 such that fluid connection is provided from internal porting 42 of preconcentrator housing 18 and internal porting 60 of sensor housing 20. In order to ensure that an airtight seal is maintained within chambers 28 and 56 while allowing contacts 36 and 58 to pass therethrough, gaskets 66 and 68 are preferably provided below preconcentrator housing 18 and sensor housing 20 respectively. Gaskets 66 and 68 thus ensure an airtight seal around contacts 36 and 58 between lower housing halves 32 and 48 and circuit board 15. Further, a bottom of contacts 36 and 58 preferably make contact with, or are otherwise soldered on or into electrical traces 74 on circuit board 15.

Figure 5:
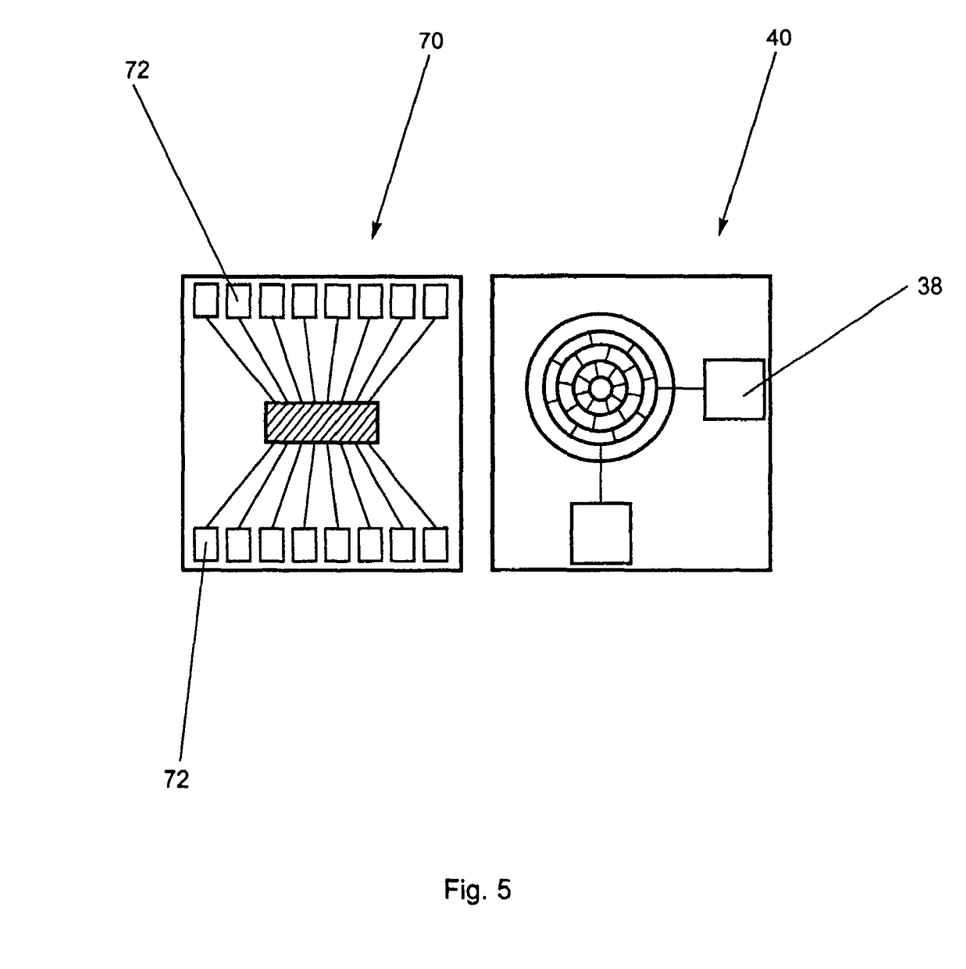
FIG. 5 is a top-view drawing illustrating embodiments of an enlarged preconcentrator and an enlarged sensor.
Figure 6:
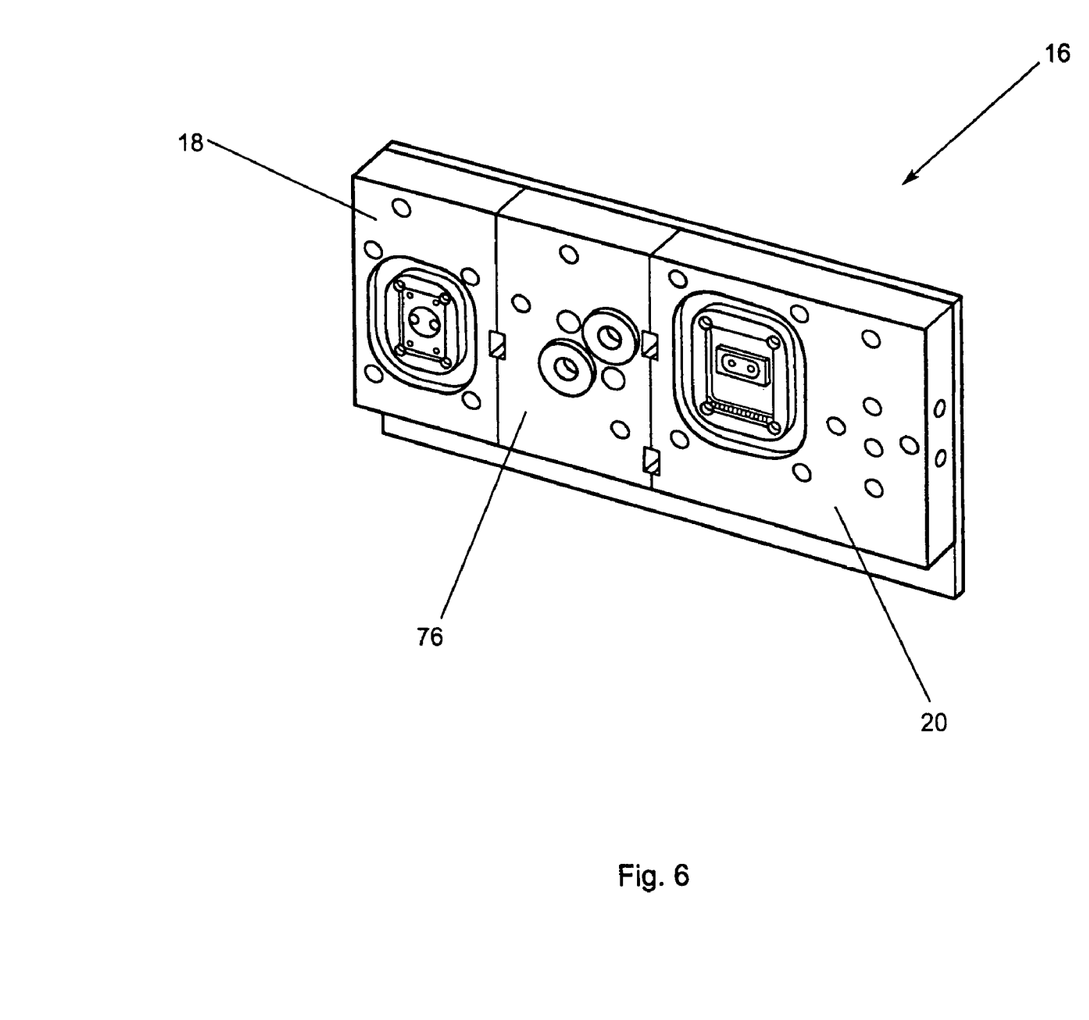
FIG. 6 is a perspective-view drawing illustrating an embodiment of the present invention wherein a gas chromatograph assembly is disposed between a preconcentrator housing and a sensor housing of the present invention.

In an embodiment of the present invention, the physical dimensions of sensor recess 54, as well as the placement of contacts 58 are maintained at a constant to ensure that sensors 70, which are preferably standing acoustic wave sensors, can be produced and distributed in quantities and with features such that the dimensions of sensor 70 enable it to be easily dropped into recess 54 and electrical pads 72 on sensor 70 can thus properly align with and provide electrical conductivity to contacts 58. As with preconcentrator 40, providing spring-loaded or otherwise resilient contacts 58 enables sensors 70 to be dropped into place with out the need for soldering, heating, or another form of connection between electrical pads 72 and contacts 58, thus further facilitating the rapidity and ease with which a sensor may be replaced.

Figure 7A:
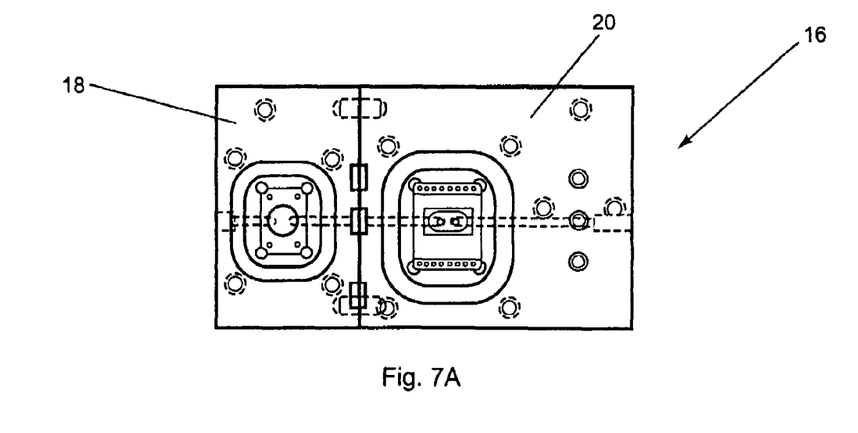
FIG. 7A is a top-view drawing schematically illustrating internal porting in accordance with an embodiment of the present invention which comprises a gas chromatograph section disposed between a preconcentrator housing and a sensor housing.

FIG. 7A illustrates a schematic-view drawing of an embodiment of the present invention depicting the fluid connection between internal portings 42 and 60 not limited to a cylinder according to an embodiment of the present invention.

Figure 7B:
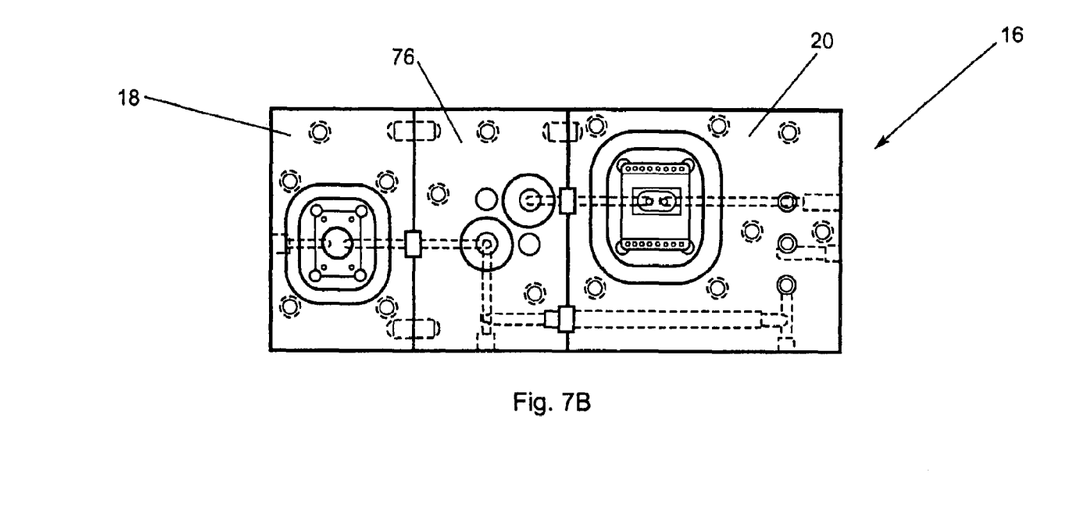
FIG. 7B is a top-view drawing schematically illustrating an embodiment of the present invention wherein a gas chromatograph section is not provided.

FIG. 7B illustrates a schematic-view drawing of an embodiment of the present invention wherein gas chromatography unit 76 is preferably provided between preconcentrator housing 18 and sensor housing 20. Accordingly, in this embodiment, the gas or liquid to be tested first passes through preconcentrator 40 then through gas chromatograph unit 76, and then through sensor housing 20.

When used to detect the presence and/or concentration of a chemical, the gas or liquid containing the chemical to be detected is first preferably passed into inlet 22 before flowing through internal porting 42 to preconcentrator 40, which is preferably housed in an air-tight environment within recess 30 contained in preconcentrator housing 18. After passing the gas or liquid through, past, or over preconcentrator 40 for a predetermined amount of time, so that the chemical to be detected can absorb therein, electricity is preferably passed through traces 74 on circuit board 15, which electricity then passes through a heating element on preconcentrator 40 via pads 38 and contacts 36. Heating preconcentrator 40 expels the chemical absorbed therein. The expelled chemical passes from preconcentrator 40, to sensor 70 via internal porting 42 and 60. In one embodiment, the expelled chemical passes through gas chromatograph section 76 before passing to sensor 70 and thereafter out outlet 62.

To rapidly replace preconcentrator 40 and/or sensor 70, in one embodiment, a user simply removes upper-housing halves 24 and/or 46 and drops preconcentrator 40 and/or sensor 70, which are preferably pre-manufactured, into recesses 30 and/or 54 respectively. The user then reattaches upper-housing halves 24 and/or 46 to lower-housing halves 32 and/or 48. Because preconcentrator 40 and sensor 70 are preferably rapidly replicable, in a preferred embodiment, electrical connection between the pads of sensor 40 and/or preconcentrator 70 can preferably be electrically connected to electrical contacts 36 and/or 58 by pressure contact alone, and thus without the need for any solder or other adhesive to be provided between a surface of the sensor and/or preconcentrator and a surface of their respective housings. Further, an individual can preferably replace a preconcentrator and/or sensor in less than about 5 minutes, and most preferably in less than about 1 minute.

Although a most preferred embodiment of the present invention comprises sensor housing 20 connectable to, but separate and distinct from preconcentrator housing 18, in an alternative embodiment, preconcentrator housing 18 and sensor housing 20 can be formed from a single-continuous piece of material with internal porting connecting housings 18 and 20. In the embodiment of the present invention which comprises gas chromatograph section 76, preconcentrator and sensor housings 18 and 20 respectively can also be incorporated into a single continuous piece of material which also comprises gas chromatograph section 76, all connected by internal porting.

Although circuit board 15 is most preferably provided, upon studying this application, those skilled in the art will readily recognize that electrical connections can be provided in other manners. For example, circuitry internal to preconcentrator housing 18, sensor housing 20, and/or gas chromatograph section 76 can be used in place of, or in conjunction with circuit board 15.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s), are hereby incorporated by reference.

What is claimed is:

1. A sensing unit comprising:
   a sensor comprising one or more electrical pads;
   a sensor housing comprising:
      internal dimensions connected to one or more ports, said internal dimensions sufficient to permit said sensor to be disposed therein;
      one or more sealing mechanisms; and
      one or more electrical contacts; and
   a preconcentrator housing.

2. The sensing unit of claim 1 wherein said preconcentrator housing comprises;
   internal dimensions connected to one or more ports, said internal dimensions sufficient to permit a preconcentrator to be disposed therein; and
   one or more electrical contacts.

3. The sensing unit of claim 2 wherein said contacts of said preconcentrator housing comprise resilient contacts.

4. The sensing unit of claim 1 wherein said internal dimensions of said preconcentrator housing are sealable from an outside environment, except for one or more ports.

5. The sensing unit of claim 1 wherein said internal dimensions are sealable from an outside environment, except for the one or more ports.

6. The sensing unit of claim 1 wherein at least one of said electrical pads of said sensor is configured in a pre-determined manner to substantially align with at least one of said electrical contacts when said sensor is disposed within said internal dimensions of said sensor housing.

7. The sensing unit of claim 1 further comprising a preconcentrator disposable within said internal dimensions of said preconcentrator housing.

8. The sensing unit of claim 7 wherein said preconcentrator comprises one or more electrical pads configured such that they substantially align with one or more electrical contacts disposed within the internal dimensions of said preconcentrator housing.

9. The sensing unit of claim 7 wherein said preconcentrator can be replaced by an individual in about a minute or less.

10. The sensing unit of claim 1 wherein said preconcentrator housing is fluidly connected to said sensor housing.

11. The sensing unit of claim 10 wherein said preconcentrator operates with only a pressure fit between said electrical pads of said preconcentrator and said contacts of said preconcentrator housing, and without the need for said pads of said preconcentrator to be soldered onto said contacts of said preconcentrator housing.

12. The sensing unit of claim 10 wherein no adhesive or sealant is used between a surface of said preconcentrator and a surface of said preconcentrator housing.

13. The sensing unit of claim 1 further comprising a gas chromatograph unit.

14. The sensing unit of claim 1 further comprising a gas chromatograph unit.

15. The sensing unit of claim 1 wherein said sensing unit operates with only a pressure fit between said electrical pads of said sensor and said contacts of said sensor housing, and without the need for said pads of said sensor to be soldered onto said contacts of said sensor housing.

16. The sensing unit of claim 1 wherein no adhesive or sealant is used between a surface of said sensor and a surface of said sensor housing.

17. The sensing unit of claim 1, wherein said sensor comprises a standing acoustic wave sensor.

18. The sensing unit of claim 1 wherein said sensor can be replaced by an individual in about a minute or less.

19. A sensing unit comprising:
   a sensor comprising one or more electrical pads; and
   a sensor housing comprising:
      internal dimensions connected to one or more ports, said internal dimensions sufficient to permit said sensor to be disposed therein;
      one or more sealing mechanisms; and
      one or more electrical contacts;
   wherein said sensor comprises a standing acoustic wave sensor.

20. The sensing unit of claim 1 wherein said electrical contacts comprise resilient contacts.

* * * * *